United States Patent
Bisagni et al.

(10) Patent No.: US 6,451,822 B1
(45) Date of Patent: Sep. 17, 2002

(54) 3-(AMINO- OR AMINOALKYL)PYRIDINONE DERIVATIVES AND THEIR USE FOR THE TREATMENT OF HIV RELATED DISEASES

(75) Inventors: Emile Bisagni; Valérie Dolle, both of Orsay; Chi Hung Nguyen, Massy; Claude Monneret, Paris; David Grierson, Buc; Anne-Marie Aubertin, Strasbourg, all of (FR)

(73) Assignees: Centre National de la Recherche Scientifique, Paris (FR); Institut Curie, Paris (FR)

(*) Notice: Subject to any disclaimer, the term of this patent is extended or adjusted under 35 U.S.C. 154(b) by 0 days.

(21) Appl. No.: 09/673,635
(22) PCT Filed: Apr. 27, 1999
(86) PCT No.: PCT/EP99/03023
§ 371 (c)(1),
(2), (4) Date: Jan. 3, 2001
(87) PCT Pub. No.: WO99/55676
PCT Pub. Date: Nov. 4, 1999

Related U.S. Application Data

(60) Provisional application No. 60/083,082, filed on Apr. 27, 1998.

(51) Int. Cl.$^7$ .................. A61K 31/4412; C07D 211/88; C07D 211/94
(52) U.S. Cl. .................. 514/349; 514/350; 514/351; 546/297; 546/298; 546/300
(58) Field of Search .................. 546/297, 298, 546/300; 514/349, 350, 351

(56) References Cited

U.S. PATENT DOCUMENTS 5,308,854 A * 5/1994 Hoffman, Jr. et al. ...... 514/338

FOREIGN PATENT DOCUMENTS

EP 0462800 * 12/1991
WO 97/05113 * 2/1997

* cited by examiner

*Primary Examiner*—Alan L. Rotman
*Assistant Examiner*—Rita Desai
(74) *Attorney, Agent, or Firm*—Oblon, Spivak, McClelland, Maier & Neustadt, P.C.

(57) ABSTRACT

The present invention is concerned with 3-(amino- or aminoalkyl)pyridinone derivatives which inhibit the reverse transcriptase of the Human Immunodeficiency Virus (HIV). It relates moreover to the use of such compounds for treating HIV-related diseases. Furthermore it relates to a process for the preparation of these compounds.

18 Claims, No Drawings

3-(AMINO- OR AMINOALKYL)PYRIDINONE DERIVATIVES AND THEIR USE FOR THE TREATMENT OF HIV RELATED DISEASES

This application is a 371 of PCT/EP99/03023 filed Apr. 27, 1999, which claims the benefit of provisional application No. 60/083,082 filed Apr. 27, 1998.

The present invention is concerned with 3-(amino- or aminoalkyl) pyridinone derivatives which inhibit the reverse transcriptase of the Human Immunodeficiency Virus (HIV).

It relates moreover to the use of such compounds for treating HIV-related diseases.

Furthermore it relates to a process for the preparation of these compounds.

It is known that some pyrimidinone and pyridinone derivatives inhibit HIV reverse transcriptase.

In particular, derivatives from 1-[(2-hydroxyethoxy)methyl]-6-(phenylthio)thymine (HEPT) are well known for their HIV1 reverse transcriptase inhibitory properties.

European Patent Application EP-0 462 800 (Merck and Company Inc.) discloses pyridinones being substituted on position 3 with an aryl or heterocyclic group, linked to the pyridinone ring through a chain.

Unfortunately, strains resistant to these compounds appeared Thus, their use in therapeutical treatments is questionable.

4-aryl-thio-pyridinones have been more recently disclosed by DOLLE et al. (1995, J. Med. Chem., 38, 4679–4686), and in the corresponding PCT Patent Application WO 97/05 113.

However, their activities are still moderate and their use in human therapy also could lead to the emergence of resistant strains.

The most active thio pyridinones disclosed therein have a 50% inhibitory concentration of virus multiplication ($IC_{50}$) for nevirapine resistant strains of about 260 nM.

The inventors have found a new pyridinone derivative family which show better HIV inhibitory properties.

They have moreover found a new process for obtaining these compounds.

The present invention relates to compounds having the following general formula I.

FORMULA (I)

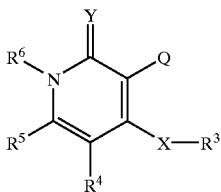

wherein
Q represents —$NR_1R_2$ or —$R_0NR_1R_2$ wherein:
$R_o$ represents $C_{1-6}$ alkanediyl;
$R_1$ and $R_2$ each independently represent $C_{1-6}$alkyl or $C_{3-6}$alkenyl; said $C_{1-6}$alkyl and $C_{3-6}$alkenyl may be substituted with one, two or three substituents selected from hydroxy, $C_{1-4}$alkyloxy, $C_{1-4}$alkylthio, aryloxy, arylthio, amino, mono- or di($C_{1-4}$alkyl)amino and aryl; or
$R_1$ and $R_2$ taken together may form a bivalent radical —$R_1$—$R_2$—wherein —$R_1$—$R_2$— represents —$(CH_2)_2$—O—$(CH_2)_2$—, —$(CH_2)_2$—$NR_7$—$(CH_2)_2$—, —$(CH_2)_2$—CH($NHR_7$)—$(CH_2)_2$— or —$(CH_2)_n$—, wherein $R_7$ represents hydrogen or $C_{1-4}$alkyl and n represents 2, 3, 4, 5 or 6;

$R_3$ represents aryl or a monocyclic or bicyclic heterocycle selected from pyridinyl, pyrimidinyl, thiazolinyl, furanyl, thienyl, imidazolyl, benzoxazolyl, benzothiazolyl, benzimidazolyl; said monocyclic or bicyclic heterocycle may optionally be substituted with one, two or three substituents each independently selected from hydroxy, $C_{1-4}$alkyl, $C_{1-4}$alkoxy, halo, trifluoromethyl, dimethylenoxy or phenyl, $R_4$ and $R_5$ each independently represent hydrogen, $C_{1-6}$alkyl, $C_{3-6}$alkenyl, $C_{1-4}$alkoxy, $C_{1-4}$alkyloxy, $C_{1-4}$alkyl, amino, mono- or di($C_{1-4}$alkyl)amino, formyl, $C_{1-4}$alkylcarbonyl, carboxyl, $C_{1-4}$alkyloxycarbonyl, or $C_{1-4}$alkylaminocarbonyl; wherein $C_{1-6}$alkyl and $C_{3-6}$alkenyl may be substituted with one, two or three substituents selected from hydroxy, $C_{1-4}$alkyloxy, $C_{1-4}$alkyl thio, aryloxy, arylthio, amino, mono- or di($C_{1-4}$alkyl)amino and aryl; or $R_4$ and $R_5$ taken together form a bivalent radical of formula —$R_4$—$R_5$— wherein —$R_4R_5$— represents —CH=CH—CH=CH— or —$(CH_2)_t$—, wherein t represents 3 or 4;

$R_6$ represents hydrogen, hydroxy, $C_{1-4}$alkyloxy, $C_{1-6}$alkyl, $C_{3-6}$alkenyl, aryl, $C_{1-4}$alkyl, amino, mono- or di($C_{1-4}$alkyl)amino or alkylaryl;

Y represents O or S;

X represents a radical of formula:

—$(CH_2)_p$—

—$(CH_2)_q$—Z —$(CH_2)_r$— or —CO— wherein
p represents 1, 2, 3, 4 or 5;
q represents 0, 1, 2, 3, 4 or 5;
r represents 0, 1, 2 or 3;
Z represents $NR_8$, C(=O), CHOH, $CHNR_8R_9$; $CF_2$, O, S or CH=CH; wherein $R_8$ and $R_9$ each independently represent hydrogen or $C_{1-4}$ alkyl; or N-oxides, stereochemically isomeric forms or a pharmaceutically acceptable addition salts thereof.

As used in the foregoing definitions and hereinafter halo defines fluoro, chloro, bromo and iodo; $C_{1-4}$-alkyl defines straight and branched chain saturated hydrocarbon radicals having from 1 to 4 carbon atoms such as methyl, ethyl, propyl, butyl and the like; $C_{1-6}$alkyl is meant to include $C_{1-4}$alkyl and the higher homologues thereof containing 5 to 6 carbon atoms such as, for example, pentyl, hexyl or the like; $C_{3-6}$alkenyl defines straight and branched chain hydrocarbon radicals containing one double bond and having from 3 to 6 carbon atoms, such as 2-propenyl, 3-butenyl, 2-butenyl, 2-pentenyl, 3-pentenyl, 3-methyl-2-butenyl and the like; and the carbon atom of said $C_{3-6}$alkenyl being connected to a nitrogen atom preferably is saturated; $C_{1-6}$alkanediyl defines bivalent straight and branched chain saturated hydrocarbon radicals having from 1 to 6 carbon atoms, such as, methylene, 1,2-ethanediyl, 1,3-propanediyl, 1,4-butanediyl, 1,5-pentanediyl, 1,6-hexanediyl and the like. The term <<C(=O)>> refers to a carbonyl group. Aryl is phenyl or phenyl substituted with one, two or three substituents selected from $C_{1-4}$alkyl, $C_{1-4}$alkyloxy, halo and trifluoromethyl, Preferred compounds according to the present invention are those in which X represents —$CH_2$— or C(=O) and $R_3$ represents a phenyl group, substituted with two methyl groups, and the most preferred of them are those wherein $R_3$ represents a phenyl group substituted, in each meta position, with two methyl groups.

Preferably, in the compounds according to the present invention, $R_1$ and $R_2$ represent each a methyl group, $R_4$ represents an ethyl group, $R_5$ represents a methyl group and/or $R_6$ represents a hydrogen atom.

The most preferred compound of this invention is the 3-dimethylamino-4-(3,5-dimethylbenzyl)-5-ethyl-6-methylpyridin-2-(1H)-one.

The compounds in which X is —$CH_2$—, $R_3$ represents a phenyl group optionally substituted, Y represents O and $R_6$ represents a hydrogen atom can be obtained by the general process represented on FIG. 1.

This first process comprises the following steps:

a) reacting a pyridine (2), substituted in position 2 with an alkoxy group and in position 3 with an amidoalkyl group, with a $C_1$–$C_6$ alkyllithium, resulting in a lithiated derivate (3) of the said pyridine.

b) transforming the lithiated derivative (3) into an organo-copper reagent by reacting it with a complex formed by Cu I and dimethyl sulphide.

c) obtaining the pyridinone (4) by reacting the organo-copper reagent with.optionally substituted benzyl halide.

d) hydrolysing the protected pyridinone (4) and obtaining the deprotected pyridinone (5).

e) substituting the 3-amine group of the pyridinone (5) and obtaining the pyridinone (6).

This first process is summarized in the reaction Scheme I hereinafter:

SCHEME I

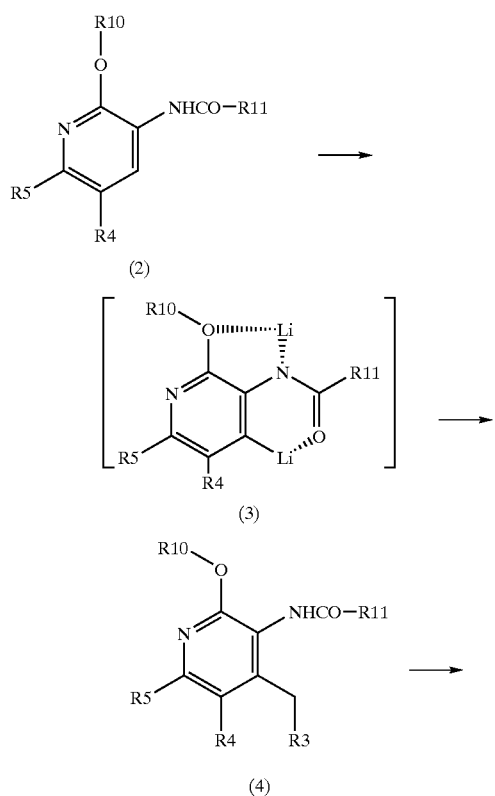

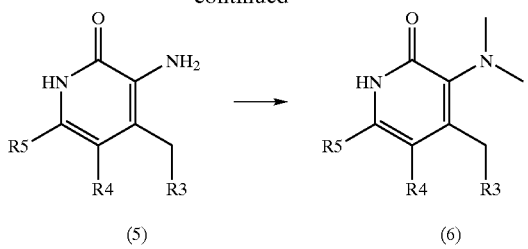

In this process $R_{10}$ and $R_{11}$ represent independently $C_1$–$C_6$ alkyl. In a preferred embodiment, $R_{10}$ is a methyl group and $R_{11}$ is a tert-butyl group.

The $C_1$–$C_6$ alkyllithium, reacted with the pyridine(2) can be a n-butyllithium.

The optionally substituted benzyl halide used in the step c) is preferably benzyl bromide.

The hydrolysis of the protected pyridinone(4), resulting in its deprotection, is advantageously obtained by adding hydrochloric acid to the pyridinone(4) and refluxing the mixture.

In a preferred embodiment, the amino group in position 3 of the pyridinone ring, deprotected during the step (d) is substituted by alkylation, by the Eschweiler-Clarke reaction.

Compounds wherein X represents —$(CH_2)_q$—Z —$(CH_2)_r$—, Y represents O, $R_3$ is an optionally substituted phenyl group and $R_6$ is an hydrogen atom can be obtained by a similar process.

Compounds wherein X represents C (=O), or —$CH_2$—, Y represents O, $R_3$ is an optionally substituted phenyl group and $R_6$ is an hydrogen atom can be obtained by a second process.

In this second process, the lithiated derivative (3) is reacted with an optionally substituted benzaldehyde, resulting in the intermediates of formula (7).

The intermediate (7) is oxidized to intermediate (8).

The intermediate (8) is thereafter deprotected by hydrolysis, as in the first process, resulting in the pyridinone (9) of general formula I.

This second process is summarized in the reaction scheme II hereinafter.

Reaction scheme II

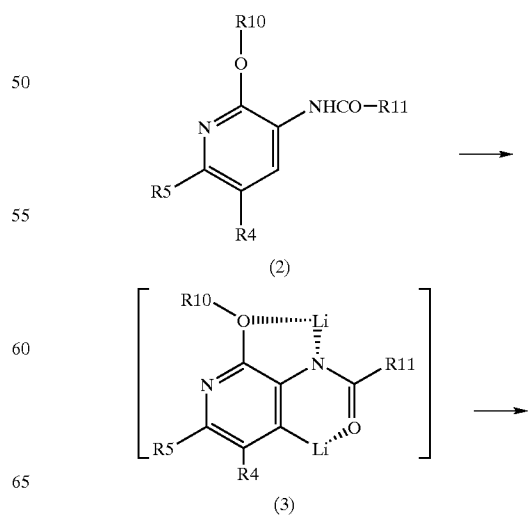

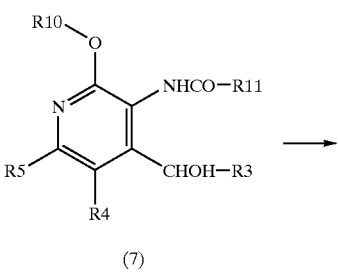

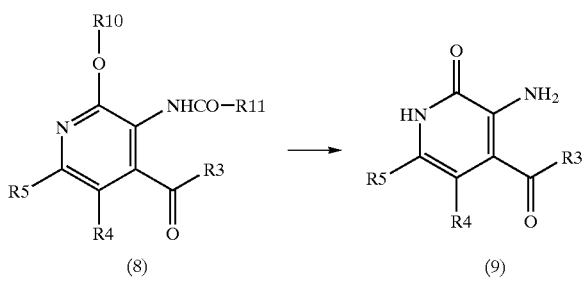

Preferably the oxidation of the intermediate (7) is performed in the presence of manganese dioxide.

The intermediate (7) can also be transformed into corresponding ester (10) wherein $R_{12}$ represents a $C_1$–$C_4$ alkyl group whose hydrogenolysis provides pyridinone(4) in better yields. Preferably, the ester (10) wherein $R_{12}$ is $CH_3$ is prepared by treatment of intermediate (7) with acetic anhydride. Subsequently hydrogenolysis is performed under hydrogen atmosphere and in the presence of a catalyst, especially 30% paladized charcoal. This process is summarized in the reaction scheme III Reaction scheme III

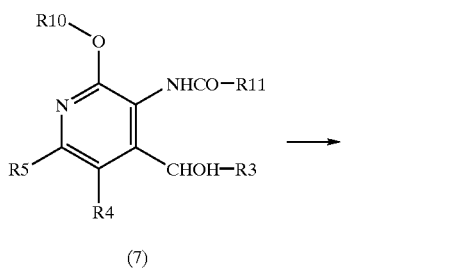

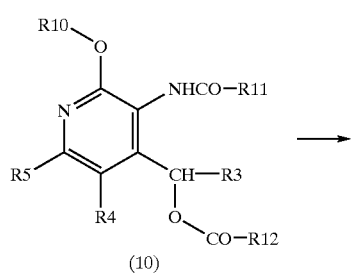

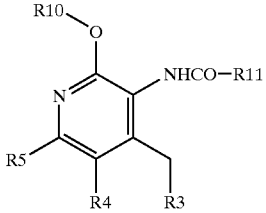

Other compounds of general formula I, and wherein X is $(CH_2)_p$ or $(CH_2)_q$—Z—$(CH_2)_r$ or C(=O), and $R_3$ is other than phenyl and $R_6$ is other than hydrogen can be obtained by these processes, appropriately adapted by the man skilled in the art.

The compounds according to the present invention, in which X is S can be obtained by the process described in the article of DOLLE et al. (1995, previously cited) or in the corresponding patent application WO 97/05 113, the contents of which are included in the present application.

The compounds can also be obtained by other processes known by the man skilled in the art.

The present invention relates moreover to the intermediates of the processes hereabove disclosed. In particular it relates to the lithiated derivative of formula (3).

The compounds of the present invention are useful in the inhibition of HIV reverse transcriptase, and in particular HIV-1 reverse transcriptase and the prevention or treatment of infection by the human immuno deficiency virus (HIV) and of HIV-related diseases, such as AIDS.

For these purposes, the compounds of the present invention may be administered orally, parenterally (including sub-cutaneous injections, intravenous, intramuscular, intrasternal injection or infusion tectoniques), by inhalation spray, or rectally, in dosage unit formulations containing pharmaceutically acceptable carriers, adjuvants and vehicles.

Thus, another object of the present invention is a method, and a pharmaceutical composition for treating HIV related diseases, HIV infection, and in particular AIDS.

The invention relates also to these compounds for use as medecine and to their use for the manufacture of a medecine for the treatment of HIV related diseases, HIV infection, and in particular AIDS.

These pharmaceutical compositions may be in the form of orally-administrable suspensions or tablets, nasal sprays, sterile injectable preparations, or suppositories.

The present invention is illustrated without being limited by the following examples.

EXAMPLES

Example 1

Preparation of 3-dimethylamino-4-(3,5-dimethylbenzyl)-5-ethyl-6-methylpyridin-2(1H)-one 1) 5-Ethyl-2-methoxy-6-methyl-3-pivaloylaminopyridine This compound has been prepared as indicated by DOLLE et al. (1997, Tetrahedron, vol. 53, n°37, 12.505–12.524). The content of this article is hereby incorporated by reference.

3,68 g of 3-Amino-5-ethyl-2-methoxy-6-methylpyridine (22,14 mmol), obtained as indicated by HOFFMAN et al. (1993, J. Med. Chem., 36, 953–966), was dissolved in a mixture of dichloromethane (260 ml) and triethylamine (3.39 ml). The mixture was cooled at 0° C. and 3.00 ml of trimethylacetyl chloride was added dropwise. The solution was stirred at 0° C. for 15 min. and then washed with 100 ml water. The aqueous layer was extracted with 3×200 ml dichloromethane. The combined organic layers were dried over magnesium sulfate and concentrated under reduced pressure. The residue was purified by column chromatography using dichloromethane as eluant to provide the 5-ethyl-2-methoxy-6-methyl-3-pivaloylaminopyridine (5.31g; 96%). Elemental analysis calculated for $C_{14}H_{22}N_2O_2$; C, 67.17, H, 8.86; N, 11.19; O, 12.78; found: C, 67.11; H, 8.56; N, 10.91; O, 12.67.

2) 4-(3,5-Dimethylbenzyl)-5-ethyl-2-methoxy-6-methyl-3-pivaloylaminopyridine i) By Lithiation of 5-ethyl-2-methoxy-6-methyl-3-pivaloylaminopyridine 5-ethyl-2-methoxy-6-methyl-3-pivaloylaminopyridine and 3,5-dimethylbenzyl bromide were dried in the presence of phosphorus pentoxide under vacuum at room temperature during 24 hours. Copper iodide ($Cu^I$) was dried in the presence of phosphorus pentoxide under vacuum at 50° C. for 24 hours. 5-ethyl-2-methoxy-6-methyl-3-pivaloylaminopyridine (1.06 g) and freshly distilled tetramethylethylenediamine (TMEDA) (2.24 mL) were dissolved in dry tetrahydrofuran (THF) (26 mL) and the mixture was cooled at −78° C. under a nitrogen atmosphere. n-Butyllithium (1.6 M in hexane, 9.26 mL) was added dropwise. The mixture was stirred for 1 hour at 0 °C.

$Cu^I$:dimethyl sulfide complex, prepared by adding dimethylsulfide (14 mL) to a suspension of copper iodide (2.82 g) in dry THF (52 ml) at −78° C. under $N_2$ atmosphere, was then added dropwise to the mixture at −78° C. The mixture was stirred at 0 °C. for 30 min and cooled again at −78° C. to allow the addition of 3,5-dimethylbenzyl bromide (3.81 g) dissolved in THF (4 mL). The resulting mixture was stirred at 0 °C. for 3 hours and at room temperature for 12 hours. 16 mL of water and 20 mL of 28% aqueous ammonium hydroxide were added. The aqueous layer was extracted with 3×80 mL of ether. The combined organic layers were washed with 40 mL of brine, dried over magnesium sulfate and concentrated under reduced pressure. The residue was purified by column chromatography using cyclohexane-ethyl acetate (1:0 to 8:2) as eluant giving 4-(3,5-dimethylbenzyl)-5-ethyl-2-methoxy-6-methyl-3-pivaloylaminopyridine (577 mg, 37%) mp 138–139° C.

ii) By Hydrogenolysis of ±(5-ethyl-2-methoxy-6-methyl-3-pivaloylaminopyridin-4-yl)-(3,5-dimethylphenyl)-methyl acetate (+, −) (5-Ethyl-2-methoxy-6-methyl-3-pivaloylaminopyridin-4-yl)-(3,5-dimethylphenyl)-methylacetate 8.34 g of (+, −)-(3,5-dimethylphenyl)-(5-ethyl-2-methoxy-6-methyl-3-pivaloylaminopyridin-4-yl)-methanol, prepared as described below, was dissolved in pyridine (200 mL) and added to acetic anhydride (10.24 mL), and the solution was stirred for 1.5 h at room temperature and for 60 h at 60° C. An additional 10.24 mL of acetic anhydride (108.51 mmol) was added and heating was continued at 60° C. for 24 h. The pyridine was evaporated under reduced pressure and the residue was taken up in 500 mL of ethyl acetate. The organic layer was washed with 170 mL of an aqueous saturated sodium bicarbonate solution, 170 mL of water and 170 mL of brine, dried over magnesium sulfate and the solvent was evaporated. The residue was purified by column chromatography using dichloromethane-ethanol (1:0 to 95:5) to give the titled compound (8.78 g, 95%) mp 70–71° C.

A mixture of this compound (850 mg) and Pd—C (30%, 850 mg) in acetic acid-water-dioxane (42.5 mL, 2:1:2, v/v/v) was stirred at room temperature for 24 hours under 10 atm of hydrogen. The catalyst was removed by filtration and washed with ethanol. The solvent of the combined filtrates was evaporated under reduced pressure giving 4-(3,5-dimethylbenzyl)-5-ethyl-2-methoxy-6-methyl-3-pivaloylaminopyridine (726 mg, 99%) which was identical to the compound as prepared in example 1.2.i).

3) 3-Amino-4-(3,5-dimethylbenzyl)-5-ethyl-6-methylpridin-2(1H)-one 3M aqueous hydrochloric acid (150 mL) was added to a suspension of 4-(3,5-dimethylbenzyl)-5-ethyl-2-methoxy-6-methyl-3-pivaloylaminopyridine (2.36 g) in water (300 mL). The mixture was refluxed for 3.5 h and then stirred at room temperature for 12 h. The solution was basified by adding concentrated ammonium hydroxyde and was extracted with 3×800 mL ethyl acetate. The combined organic layers were washed with 110 mL brine, dried over magnesium sulfate and concentrated under reduced pressure giving 3-amino-4-(3,5-dimethylbenzyl)-5-ethyl-6-methylpyridin-2(1H)-one. (1.79 g, 100%). mp 204–205° C.

4) 3-Dimethylamino-4-(3,5-dimethylbenzyl)-5-ethyl-6-methylpyridin-2-(1H)-one

To a stirred solution of 3-amino-4-(3,5-dimethylbenzyl)-5-ethyl-6-methylpyridin-2(1H)-one (200 mg) and 37% of aqueous formaldehyde (0.60 mL) in 5 mL of acetonitrile was added 139 mg of sodium cyanoborohydride. Glacial acetic acid (0.07 mL) was added dropwise and the reaction mixture was stirred at room temperature for 2 hours. An additional 0.07 mL of glacial acetic acid was added, and stirring was continued for 30 minutes. The solvent was evaporated and 15 mL ether were added to the resulting residue. The organic layer was washed with 3×30 mL 1N aqueous potassium hydroxide and 3 mL brine, dried over magnesium sulfate and concentrated under reduced pressure to give 3-dimethylamino-4-(3,5-dimethylbenzyl)-5-ethyl-6-methylpyridin-2(1H)-one (200 mg, 91%) mp 229–230° C.

Example 2

1) Biological Activity of the Compound According to Example 1

1. Material and Methods

The antiviral activity, the expression and purification of the recombinant HIV-RT enzyme, the reverse transcriptase activities and the inhibition of RT were evaluated as described in WO 97/05 113.

The retrovirucidal effect and the reverse transcription were measured as described hereinafter.

1.1. Retrovirucidal Effect

HIV-1 viral suspensions were obtained by coculture of MT4 cells and H9 cells chronically infected by HIV-$1_{Lai}$ isolate. 200 µl of a cell supernatant containing viral particles (HIV-$1_{Lai}$: 100 $TCID_{50}$) were incubated at room temperature with various concentrations of different inhibitors. After 3 hours, virions were washed through 0.02 µm anopore membrane in 1.5 mL Vectaspin tube (Whatman) for 10 minutes at 5,000 g. Each of the three subsequent washes was performed in the same conditions after the viral concentrate was refilled with 500 µL of RPMI medium. Then, the viral concentrate was readjusted to the initial volume with RPMI plus 10% foetal calf serum (FCS). The residual infectivity was assayed on P4 cells as described by CHARNEAU et al. (1994, J. Mol. Biol., 241, 651–662). Briefly, P4 cells were plated using 100 µL of DMEM medium plus 10% FCS in 96 plate multi-wells at $20\times10^5$ cells per mL. After overnight incubation at 37° C., the supernatant was discarded and the viral preparation (200 μL) was added. One day later the wells were washed three times in PBS. Each well was refilled with 200 μL of a reaction buffer containing 50 mM Tris-HCl pH 8.5, 100 mM 2-mercaptoethanol, 0.05% Triton X-100 and 5 mM 4-methylumbelliferyl β-D-galactopyranoside (MUG). After 3 hours at 37° C., the level of the reaction was measured in a fluorescence microplate reader.

1.2) Reverse Transcription

The plasmid pAV4 containing the 50-997 HIV-1 nucleotide fragment (MAL strain) in pSP64, under the control of the bacteriophage T7 promoter was a kind gift from Dr. J. L. DARLIX (INSERM-Lyon, France). *E. coli* HB 101 recA⁻ was used for plasmid amplification. After digestion of this clone with PstI and in vitro transcription using T7 RNA polymerase, a HIV-1 genomic RNA fragment starting at position +50 of the MAL sequence was obtained. In vitro transcription using T7 RNA polymerase as performed as follows. Three μg of linearized plasmid DNA were transcribed in 100 μL of 40 mM Tris-HCl pH 8.O, 8 mM $MgCl_2$, 10 mM spermidine, 25 mM NaCl, 10 mM dithiothreitol, 0.5 mM of each ribonucleoside triphosphate, with 100 units of T7 RNA polymerase and in the presence of 20 units of human placenta ribonuclease inhibitor, for 2 hours at 37° C. After treatment with 12 units of Rnase-free Dnase I (for 10 minutes at 37° C.), the RNA transcripts were extracted with 1 volume of phenol/chloroform/isoamyl alcohol (24:24:I) and with chloroform and precipitated in 2.5 volumes of ethanol and 0.3 M ammonium acetate (pH 5.5).

Reverse transcription was performed in a total volume of 50 μL containing 50 mM Tris-HCl pH 8.0, 6 mM $MgCl_2$, 2 mM dithiothreitol, 12 mM NaCl, 150 nM HIV-1 RNA, and either 200 nM of a synthetic oligodeoxynucleotide primer (18-mer ODN) complementary to the PBS of HIV-1 RNA, or 200 nM $tRNA^{Lys3}$. When the 18-mer ODN was used as primer, incubation was carried out at 37° C. with the template and 300 nM RT. After 30 minutes, 10μ Ci [($\alpha$-$^{32}$P] dGTP (3000 Ci/mmol) and 0.1 mM of each dNTP were added and the incubation proceeded for 30 minutes at 37° C. With $tRNA^{Lys3}$ as primer, the same conditions were used except that tRNA and RNA were prehybridized by heating for 2 minutes at 90° C. and then slowly cooled. Samples were extracted with phenol-chloroform and collected by ethanol precipitation. Reaction products were analyzed on 8% polyacrylamide-TBE (90 mM Tris pH 8.3, 90 mM borate, 2 mM EDTA)-7 M urea gels.

Results

The antiviral activity of the compounds according to example 1 has been tested on various strains.

On HIV-LAI wild type this compound shows the following activities:

IC50=0.2 nM; CC50>10⁵ nM (S.I.>33.333).

On an HIV-1 novirapine resistant strain the activities of the compound of example 1 are as follows:

$IC_{50}$>10⁴nM $CC_{50}$>10⁴nM

The compound of example 1 has been also tested on various HIV strains and primary cell cultures. The table 1 illustrates the activity of this compound on these strains.

The retrovirucidal effect of the compound according to example 1 has been tested. Table 2 illustrates this effect at various doses of this compound.

The $IC_{50}$ of the compound of example 1 for the inhibition of the reverse transcriptase is 20 nM.

TABLE 1

Anti-HIV-1 activity of the compound of example 1 on various HIV strains and primary cell cultures
$IC_{50}$(nM)/$CC_{50}$(nM)

| Compound | HIV-1 IIIB/ MT4 | HIV-1 AZTres./ MT4 | HIV-1 IIIB/ PBMC | HIV-2 D 194/ PBMC | HIV-1 Bal/Mono/ macrophages |
|---|---|---|---|---|---|
| Example 1 | 2.4/>1000 | 0.2/>1000 | 0.58/>1000 | >1000/>1000 | 0.004/>1000 |

TABLE 2

Inhibition of infectivity of the compound of example 1

| Dosage of compound of example 1 | % inhibition of infectivity |
|---|---|
| 10 nM | 26% |
| 100 nM | 46% |
| 1 μm | 83% |
| 10 μm | 99% |

Example 3

Other 3-(amino- or aminoalkyl)pyridinone Derivatives and Their Retrovirucidal Activity Against Two Different HIV-1 Strains 3.1 Compounds Further compounds according to the general formula (I) (compounds n°1–25, 27–108, 110–125, 127–145 and 147–203) as well as four intermediate compounds used for synthesis (compounds n°26, 109, 126 and 146) have been synthesized and are listed in table 3 below.

The meaning of each of the groups Y, Q and R3–R6 is defined for every exemplified pyridinone derivative.

3.2 Retrovirucidal Effect

The retrovirucidal effect of each pyridinone derivative listed in table 3 has been assayed according to the teachings of example 2, excepted that the anti-viral effect has been tested on the two following HIV-1 strains:

a) HIV-1 strain IIIB (see example 2);

b) HIV-1 strain 103 N which is a mutant strain bearing a point mutation in the reverse transcriptase gene leading to an enzyme wherein the initial Lys-103 residue is replaced for a Asn residue.

HIV-1 103N strain exhibits resistance to the reverse transcriptase inhibitor TIBO R82913 (BALZARINI J. et al. 1993, Virology, 192: 246–253). The HIV-1 103 N strain has also been described by SAHLBERG et al.,(1998, Antiviral Res., 37 (3): ASS) and BALZARINI et al. (1996, Antimicrobial Agents and Chemotherapy, 40 (6): 1454–1466).

The results are expressed as $pIC_{50}$ ($pIC_{50}$=−log $IC_{50}$), of every of compound as regards to each of the HIV-1 strains IIIB and 103N. Thus, the $pIC_{50}$ value of compound n°1 as regards to HIV-1 IIIB being 7,6999, the $IC_{50}$ can be directly deduced as being equal to $10^{-7,6999}$M.

Such high retrovirucidal activities had never been observed previously when using prior art reverse transcriptase inhibitors.

Consequently, the novel pyridinone derivatives according to the present invention are of a high therapeutical value against HIV related diseases, particularly against HIV-1 related diseases.

TABLE 3
| | Y | Q | X–R3 | R4 |
|---|---|---|---|---|
| 3 | O | NMe2 | 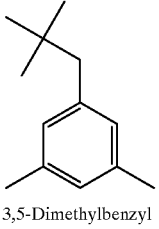<br>3,5-Dimethylbenzyl | Et |
| 4 | O | 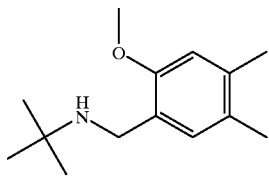<br>Chemistry 33 | 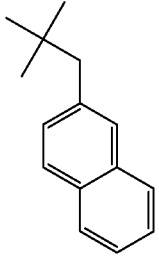<br>3,5-Dimethylbenzyl | Et |
| 10 | O | NMe2 | 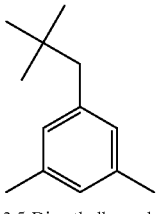<br>Chemistry 82 | Et |
| 11 | O | NMe2 | 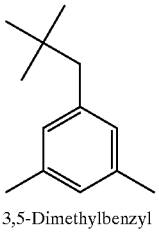<br>3,5-Dimethylbenzyl | Et |
| 12 | O | NEt2 | 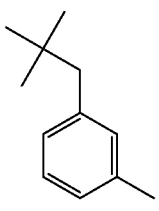<br>3,5-Dimethylbenzyl | Et |
| 13 | O | NMe2 | <br>3-Methylbenzyl | Et |

TABLE 3-continued
| | | | | | |
|---|---|---|---|---|---|
| 14 | O | NMe2 | 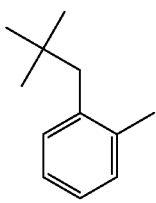 2-Methylbenzyl | | Et |
| 16 | O | NMe2 | 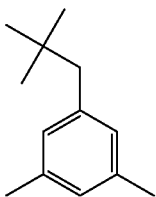 3,5-Dimethylbenzyl | | H |
| 17 | O | N(n-Pr)2 | 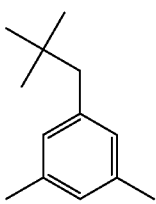 3,5-Dimethylbenzyl | | Et |
| 18 | O | NMe2 | 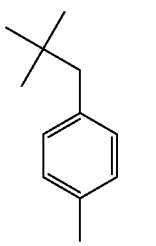 4-Methylbenzyl | | Et |
| 19 | O | NMe2 | 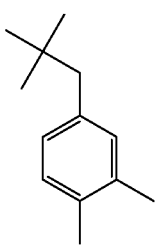 3,4-Dimethylbenzyl | | Et |
| 20 | O | NMe2 | 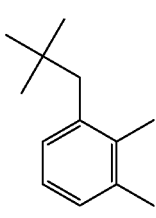 2,3-Dimethylbenzyl | | Et |

TABLE 3-continued
| | | | | | |
|---|---|---|---|---|---|
| 21 | O | NMe2 | 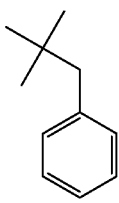  Benzyl | | Et |
| 22 | O | NMe2 | 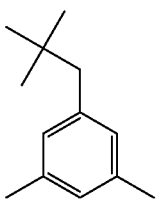  3,5-Dimethylbenzyl | | Et |
| 23 | O | NMe2 | 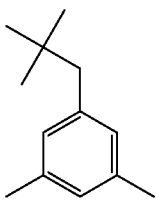  3,5-Dimethylbenzyl | | Et |
| 24 | O | 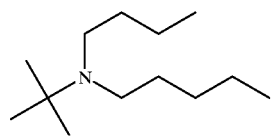  Chemistry 165 | 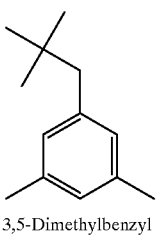  3,5-Dimethylbenzyl | | Et |
| 25 | O | 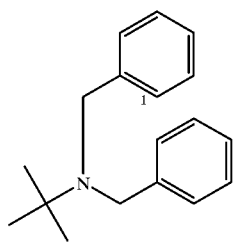  Chemistry 171 | 3,5-Dimethylbenzyl | | Et |
| 26 | O | 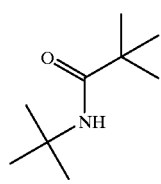  Chemistry 177 | 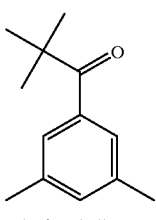  3,5-Dimethylbenzoyl | | Et |

TABLE 3-continued
| 28 | O | NMe2 | 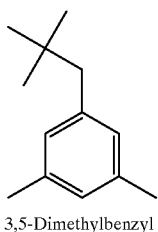3,5-Dimethylbenzyl | Et |
| --- | --- | --- | --- | --- |
| 29 | O | NHCH2Ph | 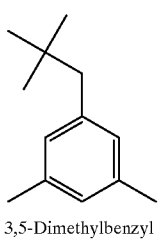3,5-Dimethylbenzyl | Et |
| 30 | O | 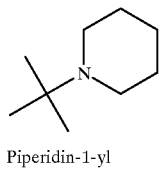Piperidin-1-yl | 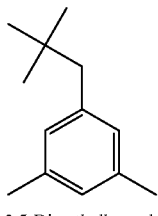3,5-Dimethylbenzyl | Me |
| 33 | O | NMe2 | 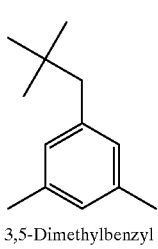3,5-Dimethylbenzyl | Me |
| 34 | O | NMe2 | 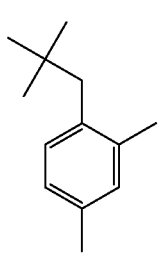2,4-Dimethylbenzyl | Et |
| 35 | O | NMe2 | 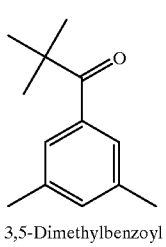3,5-Dimethylbenzoyl | Et |

TABLE 3-continued
| 36 | O | 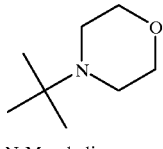 N-Morpholino | 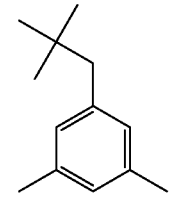 3,5-Dimethylbenzyl | Et |
| --- | --- | --- | --- | --- |
| 37 | O | NMe2 | 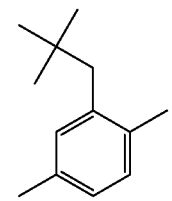 2,5-Dimethylbenzyl | Et |
| 38 | O | NMe2 | 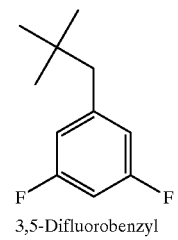 3,5-Difluorobenzyl | Et |
| 40 | O | NMe2 | 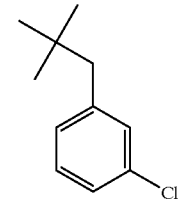 3-Chlorobenzyl | Et |
| 42 | O | NMe2 | 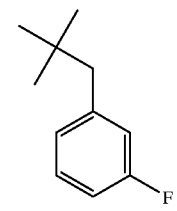 3-Fluorobenzyl | Et |
| 43 | O | NMe2 | 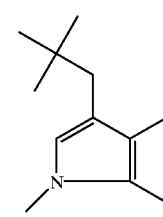 Chemistry 280 | Et |

TABLE 3-continued
| | | | | | |
|---|---|---|---|---|---|
| 44 | O | NMe2 | 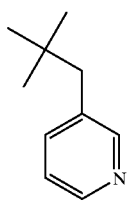\n\nChemistry 288 | | Et |
| 45 | O | NMe2 | 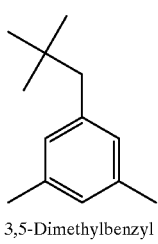\n\n3,5-Dimethylbenzyl | | Et |
| 47 | O | 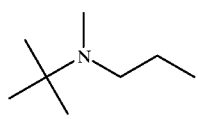\n\nChemistry 303 | 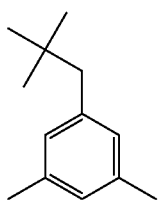\n\n3,5-Dimethylbenzyl | | Et |
| 48 | O | NMe2 | 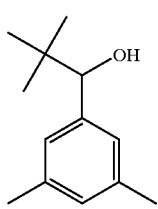\n\nChemistry 310 | | Et |
| 51 | O | NMe2 | 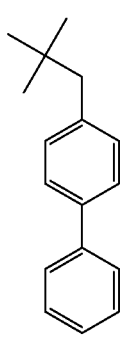\n\nChemistry 534 | | Et |

TABLE 3-continued
| 53 | O | NMe2 | 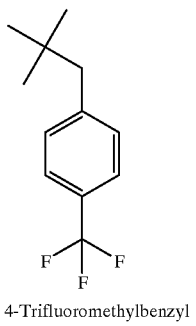 4-Trifluoromethylbenzyl | Et |
| --- | --- | --- | --- | --- |
| 55 | O | NMe2 | 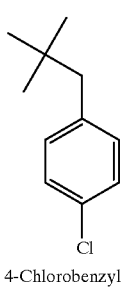 4-Chlorobenzyl | Et |
| 56 | O | 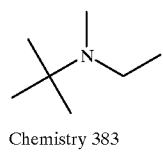 Chemistry 383 | 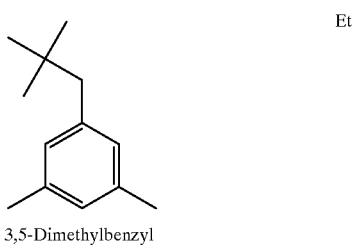 3,5-Dimethylbenzyl | Et |
| 57 | O | NMe2 | 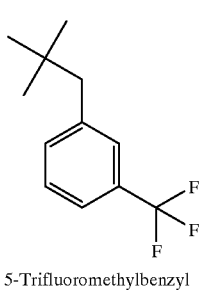 5-Trifluoromethylbenzyl | Et |
| 59 | O | NMe2 | 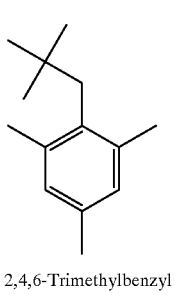 2,4,6-Trimethylbenzyl | Et |

TABLE 3-continued
| 60 | O | NMe2 | 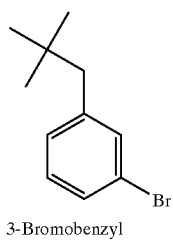<br>3-Bromobenzyl | Et |
| --- | --- | --- | --- | --- |
| 61 | O | 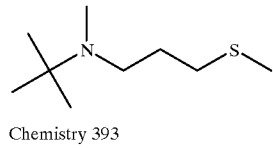<br>Chemistry 393 | 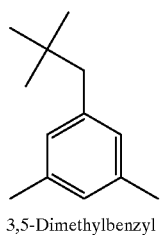<br>3,5-Dimethylbenzyl | Et |
| 62 | O | 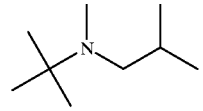<br>Chemistry 395 | 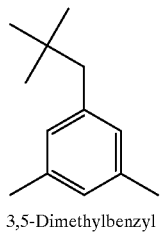<br>3,5-Dimethylbenzyl | Et |
| 63 | O | NMe2 | 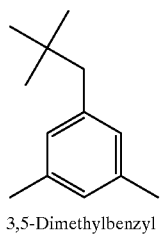<br>3,5-Dimethylbenzyl | Me |
| 65 | O | NMe2 | 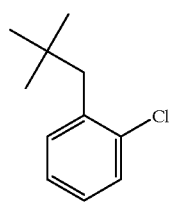<br>2-Chlorobenzyl | Et |
| 66 | O | NMe2 | 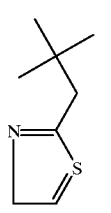<br>Chemistry 430 | Et |

TABLE 3-continued
| | | | | |
|---|---|---|---|---|
| 67 | O | 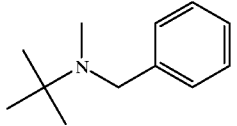<br>Chemistry 435 | 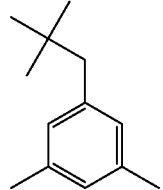<br>3,5-Dimethylbenzyl | Et |
| 68 | O | 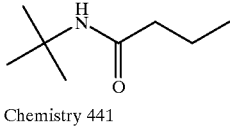<br>Chemistry 441 | 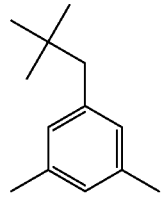<br>2,5-Dimethylbenzyl | Et |
| 70 | O NMe2 | | 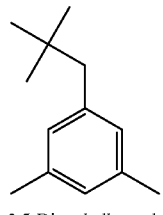<br>3,5-Dimethylbenzyl | 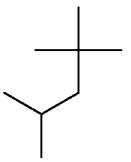<br>Chemistry 45 |
| 71 | O NMe2 | | 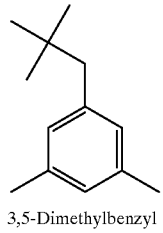<br>3,5-Dimethylbenzyl | n-Pr |
| 72 | O | 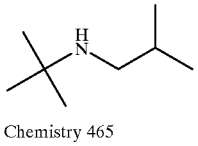<br>Chemistry 465 | 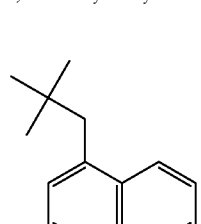<br>3,5-Dimethylbenzyl | Et |
| 75 | O NMe2 | | <br>Chemistry 490 | Et |

TABLE 3-continued
| 77 | O | NMe2 | 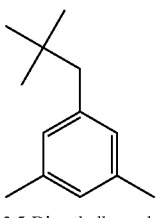 3,5-Dimethylbenzyl | H |
| --- | --- | --- | --- | --- |
| 78 | O | 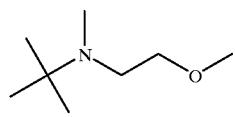 Chemistry 807 | 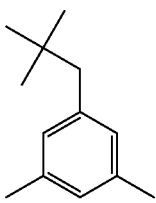 3,5-Dimethylbenzyl | Et |
| 79 | O | 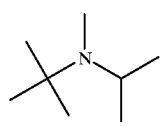 Chemistry 813 | 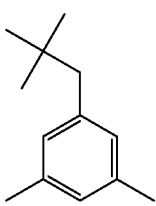 3,5-Dimethylbenzyl | Et |
| 82 | O | 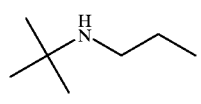 Chemistry 531 | 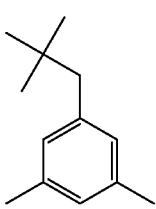 3,5-Dimethylbenzyl | Et |
| 86 | O | NMe2 | 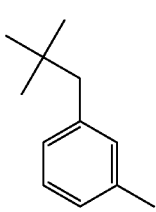 3-Methylbenzyl | Me |
| 88 | O | NMe2 | 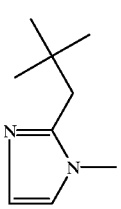 Chemistry 568 | Et |

TABLE 3-continued
| | | | | |
|---|---|---|---|---|
| 90 | O | NMe2 | 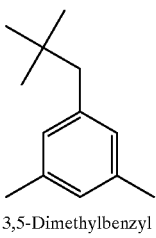<br>3,5-Dimethylbenzyl | H |
| 92 | O | NMe2 | 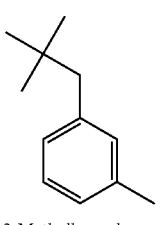<br>3-Methylbenzyl | (CH2)4 |
| 93 | O | NMe2 | 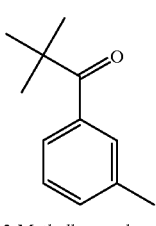<br>3-Methylbenzoyl | Et |
| 95 | O | NEt2 | 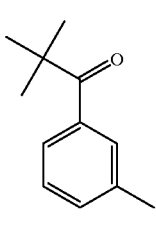<br>3-Methylbenzoyl | Et |
| 96 | O | NMe2 | 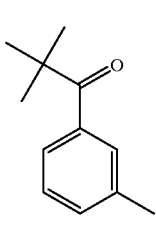<br>3-Methylbenzoyl | Me |
| 99 | O | NMe2 | 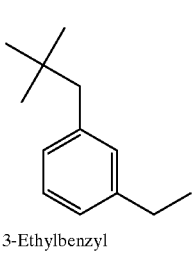<br>3-Ethylbenzyl | Et |

TABLE 3-continued
| 101 | O | NMe2 | 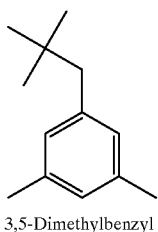<br>3,5-Dimethylbenzyl | H |
| --- | --- | --- | --- | --- |
| 102 | O | NMe2 | 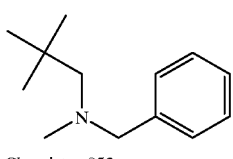<br>Chemistry 852 | Et |
| 104 | O | NMe2 | 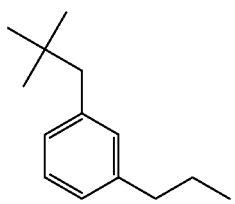<br>Chemistry 864 | Et |
| 106 | O | NMe2 | 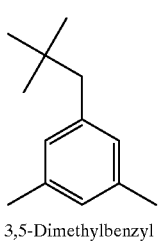<br>3,5-Dimethylbenzyl | Cl |
| 107 | O | NMe2 | 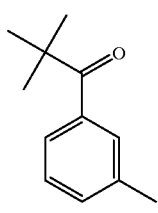<br>3-Methylbenzoyl | (CH2)4 |
| 108 | O | NMe2 | 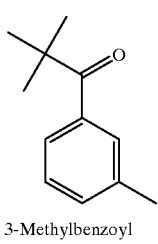<br>3-Methylbenzoyl | Me |

TABLE 3-continued
| 109 | O | 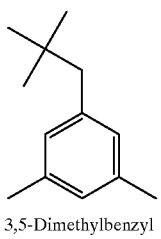 Chemistry 699 | 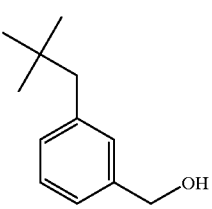 3,5-Dimethylbenzyl | H |
| --- | --- | --- | --- | --- |
| 110 | O | NMe2 | 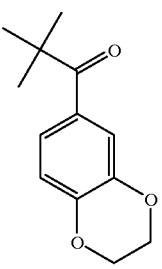 Chemistry 708 | Et |
| 112 | O | NMe2 | 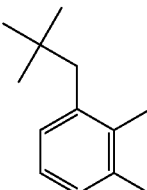 Chemistry 718 | Et |
| 114 | O | 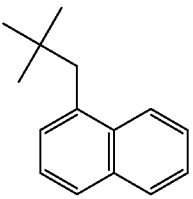 Chemistry 729 | 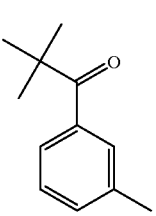 Chemistry 730 | Et |
| 115 | O | NMe2 | 3-Methylbenzoyl | Et |
| 116 | O | NMe2 | 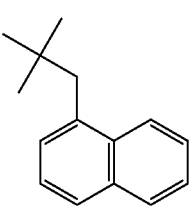 Chemistry 748 | Et |

TABLE 3-continued
| 117 | O | CH2NMe2 | 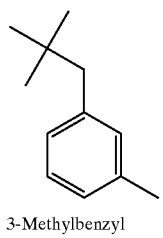 3-Methylbenzyl | (CH2)4 |
| --- | --- | --- | --- | --- |
| 119 | O | NMe2 | 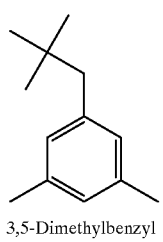 3,5-Dimethylbenzyl | Me |
| 121 | O | NMe2 | 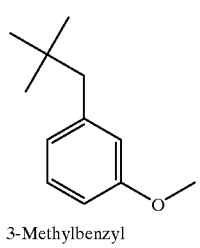 3-Methylbenzyl | Et |
| 122 | O | NMe2 | 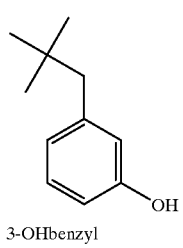 3-OHbenzyl | Et |
| 123 | O | 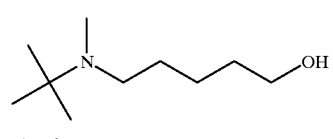 Chemistry 789 | 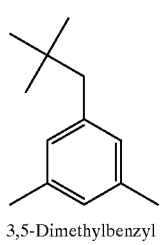 3,5-Dimethylbenzyl | Et |
| 127 | O | NMe2 | 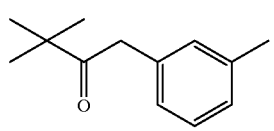 Chemistry 814 | Et |

TABLE 3-continued

| 128 | O | NMe2 | [Chemistry 820: 1-(3-(hydroxymethyl)phenyl)-2,2-dimethylpropan-1-one] | Et |
| 129 | O | [Chemistry 825: N-tert-butyl-N-methyl-1-methoxypropan-2-amine] | 3,5-Dimethylbenzyl | Et |
| 132 | O | NMe2 | 3-Methylbenzyl | (CH2)3 |
| 133 | O | NMe2 | [Chemistry 850: N-neopentyl-N-methyl-3,5-dimethylaniline] | Et |
| 135 | O | NMe2 | [Chemistry 862: neopentyl-benzodioxine] | Et |
| 136 | O | [N-tert-butyl-N-methyl-2-methoxyethanamine] | 3-Methylbenzyl | Et |

TABLE 3-continued
| 137 | S | NMe2 | 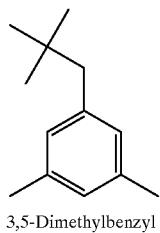  3,5-Dimethylbenzyl | Et |
| 138 | S | NMe2 | 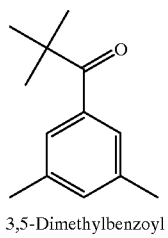  3,5-Dimethylbenzoyl | Et |
| 143 | O | NMe2 | 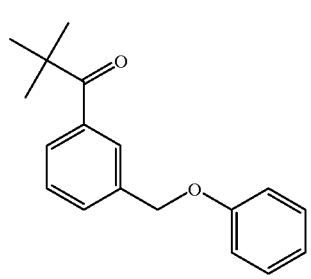  Chemistry 910 | Et |
| 144 | O | 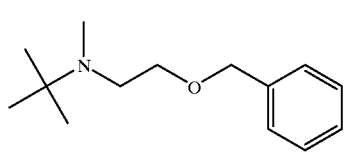  Chemistry 913 | 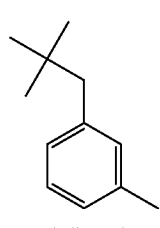  3-Methylbenzyl | Et |
| 145 | O | 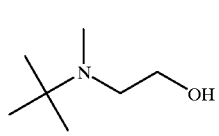  Chemistry 921 | 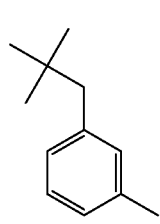  3-Methylbenzyl | Et |
| 146 | O | 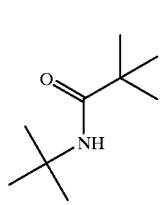  Chemistry 927 | 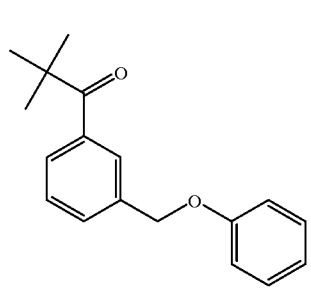  Chemistry 928 | Et |

TABLE 3-continued
| 147 | O | NMe2 | 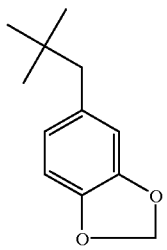 Chemistry 934 | Et |
| 148 | O | NMe2 | 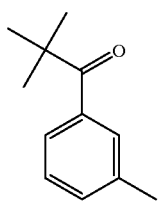 3-Methylbenzoyl | (CH2)3 |
| 149 | O | NMe2 | 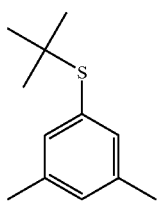 Chemistry 948 | Et |
| 151 | O | NMe2 | 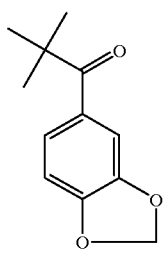 Chemistry 958 | Et |
| 152 | O | NMe2 | 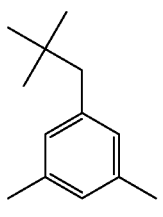 3,5-Dimethylbenzyl | Et |
| 153 | O | NMe2 | 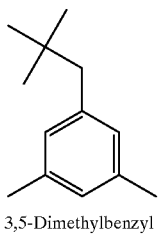 3,5-Dimethylbenzyl | Et |

TABLE 3-continued
| 154 | O | 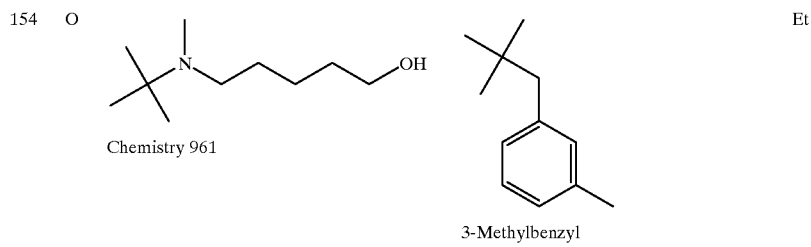Chemistry 961 | 3-Methylbenzyl | Et |
| 155 | O | 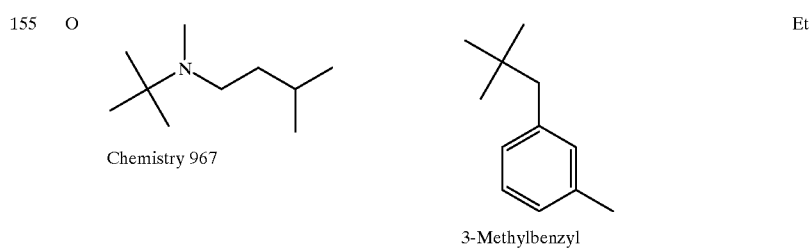Chemistry 967 | 3-Methylbenzyl | Et |
| 157 | O | NMe2 | 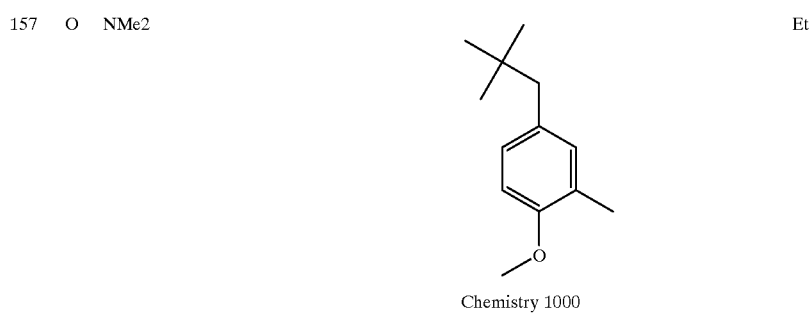Chemistry 1000 | Et |
| 158 | O | NMe2 | 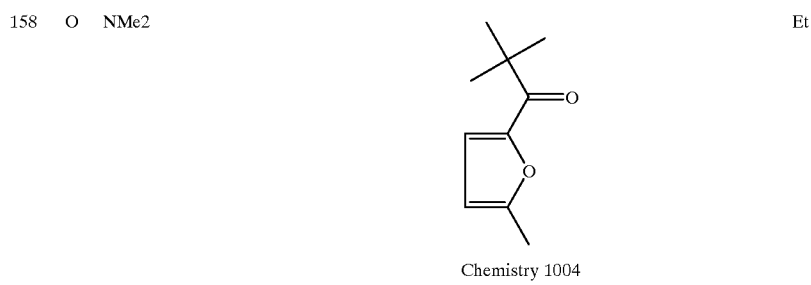Chemistry 1004 | Et |
| 160 | O | NMe2 | 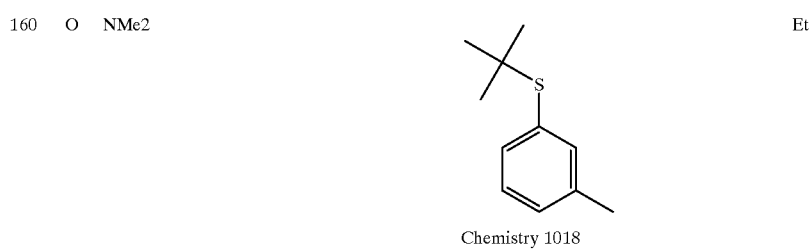Chemistry 1018 | Et |

TABLE 3-continued
| 161 | O | 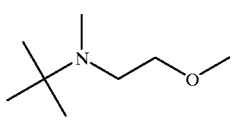 Chemistry 1023 | 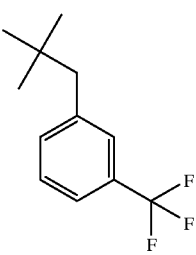 5-Trifluoromethylbenzyl | Et |
| --- | --- | --- | --- | --- |
| 162 | O | NMe2 | 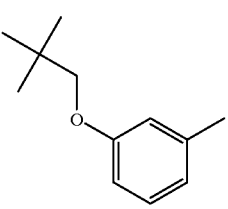 Chemistry 1030 | Et |
| 163 | O | NMe2 | 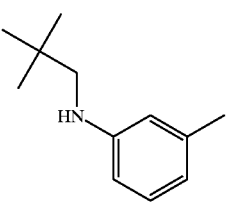 Chemistry 1036 | Et |
| 164 | O | 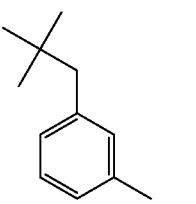 Chemistry 1041 | 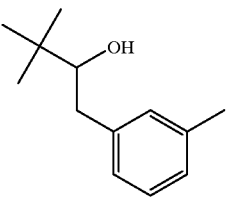 3-Methylbenzyl | Et |
| 165 | O | NMe2 | 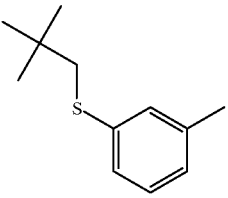 Chemistry 1048 | Et |
| 166 | O | NMe2 |  Chemistry 1054 | Et |

TABLE 3-continued
| 167 | O | NMe2 | 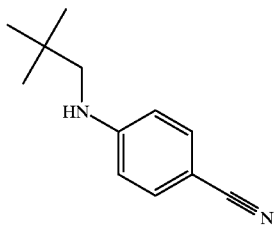<br>Chemistry 1050 | Et |
| 169 | O | NMe2 | 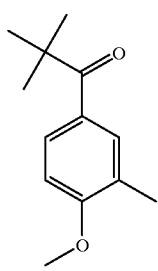<br>Chemistry 1072 | Et |
| 170 | O | NMe2 | 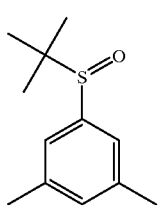<br>Chemistry 1078 | Et |
| 171 | O | NMe2 | 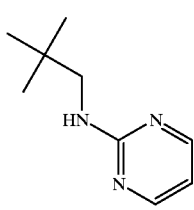<br>Chemistry 1084 | Et |
| 173 | O | NMe2 | 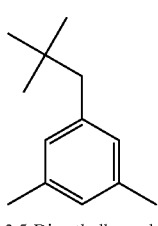<br>3,5-Dimethylbenzyl | (CH2)4 |
| 174 | O | NMe2 | 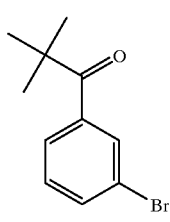<br>3-Bromobenzoyl | Et |

TABLE 3-continued
| | | | | |
|---|---|---|---|---|
| 175 | O | 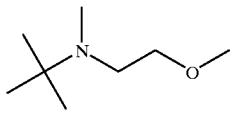<br>Chemistry 1107 | 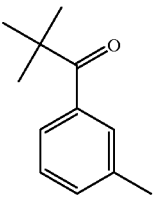<br>3-Methylbenzoyl | Et |
| 176 | O | NMe2 | 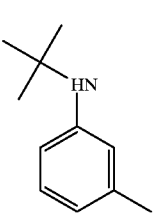<br>Chemistry 1114 | Et |
| 178 | O | NMe2 | 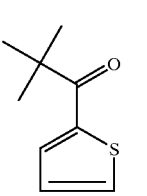<br>Chemistry 1126 | Et |
| 180 | O | 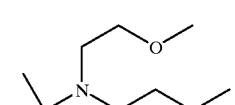<br>Chemistry 1137 | 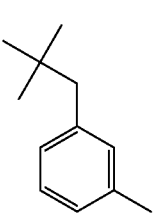<br>3-Methylbenzyl | Et |
| 181 | O | NMe2 | 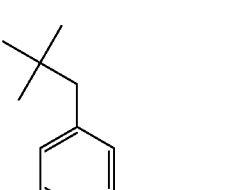<br>Chemistry 1150 | Et |
| 183 | O | NMe2 | 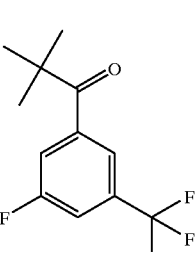<br>Chemistry 1182 | Et |

TABLE 3-continued

| # | | | | |
|---|---|---|---|---|
| 184 | O | Chemistry 1167 | 3-Bromobenzyl | Et |
| 185 | O | Chemistry 1173 | 3-Bromobenzoyl | Et |
| 187 | O | NMe2 | Chemistry 1186 | Et |
| 191 | O | NMe2 | 3,5-Dichlorobenzyl | Et |
| 192 | O | NMe2 | 3,4-Dichlorobenzoyl | Et |
| 193 | O | NMe2 | Chemistry 1222 | Et |

TABLE 3-continued
| | | | | |
|---|---|---|---|---|
| 195 | O | 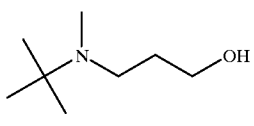<br>Chemistry 1233 | 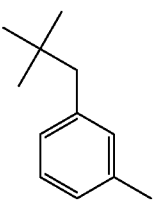<br>3-Methylbenzyl | Et |
| 196 | O | NMe2 | 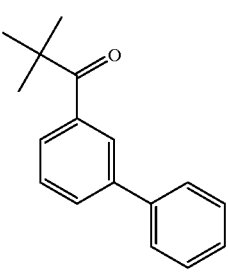<br>Chemistry 1240 | Et |
| 199 | O | 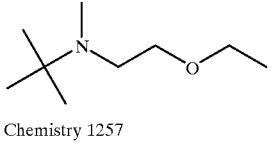<br>Chemistry 1257 | 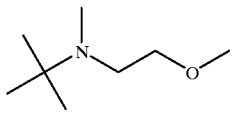<br>3-Methylbenzyl | Et |
| 200 | O | 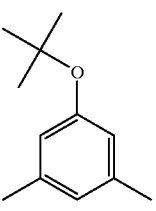<br>Chemistry 1263 | 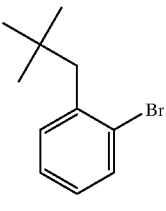<br>Benzyl | Et |
| 201 | O | NMe2 | <br>Chemistry 1276 | Et |
| 203 | O | NMe2 | <br>2-Bromobenzyl | Et |

TABLE 3-continued
|  | R5 | R6 | HIV1 pIC50 | |
|---|---|---|---|---|
|  |  |  | strain 111D | strain 103N |
| 3 | Me | H | 8.004 | 7.438 |
| 4 | Me | H | 5.094 | <4 |
| 10 | Me | H | 6.241 | 4.389 |
| 11 | Me | Me | 7.215 | 6.084 |
| 12 | Me | H | 8.022 | 6.383 |
| 13 | Me | H | 9.824 | 7.822 |
| 14 | Me | H | 7.676 | 5.849 |
| 16 | H | H | 5.061 | 4.401 |
| 17 | Me | H | 6.285 | 4.379 |
| 18 | Me | H | 6.454 | 4.895 |
| 19 | Me | H | 7.447 | 5.847 |
| 20 | Me | H | 6.926 | 5.585 |
| 21 | Me | H | 8.409 | 6.53 |
| 22 | Me | Benzyl | 4.503 | <4 |
| 23 | Me | 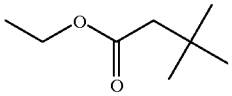 Chemistry 163 | 5.254 | <4 |
| 24 | Me | H | 4.262 | <4 |
| 25 | Me | H | <4 | 4.259 |
| 26 | Me | H |  |  |
| 28 | Et | H | 8.032 | 5.943 |
| 29 | Me | H | 8.555 | 6.494 |
| 30 | Me | H | 6.214 | 4.224 |
| 33 | Me | H | 8.42 | 6.288 |
| 34 | Me | H | 5.019 | <4 |
| 35 | Me | H | 8.585 | 7.987 |
| 36 | Me | H | 6.763 | <4 |
| 37 | Me | H | 8.796 | 5.729 |
| 38 | Me | H | 8.155 | 7.402 |
| 40 | Me | H | 8.585 | 7.412 |
| 42 | Me | H | 8.569 | 7.18 |
| 43 | Me | H | 7.377 | 6.422 |
| 44 | Me | H | 7.889 | 8.255 |
| 45 | Me | Et | 8.519 | 4.095 |
| 47 | Me | H | 7.767 | 6.968 |
| 48 | Me | H | 8 | 6.711 |
| 51 | Me | H | 5.384 | <5 |
| 53 | Me | H | 5.826 | <5 |
| 55 | Me | H | 5.651 |  |
| 56 | Me | H | 8.194 | 7.11 |
| 57 | Me | H | 8.086 | 6.414 |
| 59 | Me | H | 6.029 | <5 |
| 60 | Me | H | 5.444 | 7.001 |
| 61 | Me | H | 7.693 | 6.922 |
| 62 | Me | H | 8.604 | 5.305 |
| 63 | n-Pr | H | 7.029 | 8.334 |
| 65 | Me | H | 8.284 | 6.405 |
| 66 | Me | H | 7.583 | 5.72 |
| 67 | Me | H | 6.804 | 4.955 |
| 68 | Me | H |  |  |
| 70 | Me | H | 7.762 | 7.159 |
| 71 | Me | H | 7.777 | 7.049 |
| 72 | Me | H | 7.079 | <4 |
| 75 | Me | H | 5.252 | 4.132 |
| 77 | i-Am | H | 5.827 | <4 |
| 78 | Me | H | 8.678 | 7.128 |
| 79 | Me | H | 6.987 | 5.47 |
| 82 | Me | H | 7.735 | 6.813 |
| 86 | Me | H | 7.863 | 5.936 |
| 88 | Me | H | <4 |  |
| 90 | n-Bu | H | 6.359 |  |
| 92 | (CH2)4 | H | 7.807 |  |
| 93 | Me | H | 8.721 |  |
| 95 | Me | H | 8.265 |  |
| 96 | Me | H | 7.624 | 6.37 |
| 99 | Me | H | 8.569 | 6.715 |
| 101 | Me | H | 6.341 | 4.25 |
| 102 | Me | H | 4.369 | <4 |

TABLE 3-continued
| | | | | |
|---|---|---|---|---|
| 104 | Me | H | 8 | 7.059 |
| 106 | H | H | 7.063 | |
| 107 | (CH2)4 | H | 7.231 | |
| 108 | Et | H | 7.005 | |
| 109 | OMe | H | | |
| 110 | Me | H | 7.783 | |
| 112 | Me | H | 6.384 | |
| 114 | Me | H | | |
| 115 | Me | 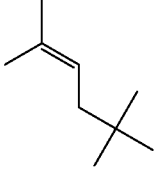 | <4.307 | |
Chemistry 745
| | | | | |
|---|---|---|---|---|
| 116 | Me | H | 6.527 | |
| 117 | (CH2)4 | H | <4.139 | |
| 119 | i-Pr | H | 6.114 | |
| 121 | Me | H | 8.468 | 6.948 |
| 122 | Me | H | 7.196 | |
| 123 | Me | H | 8.444 | 6.916 |
| 127 | Me | H | 4.174 | |
| 128 | Me | H | 7.848 | |
| 129 | Me | H | 8.398 | 7.057 |
| 132 | (CH2)3 | H | 7.563 | |
| 133 | Me | H | 4.94 | |
| 135 | Me | H | 6.688 | |
| 136 | Me | H | 9 | 6.998 |
| 137 | Me | H | 7.658 | |
| 138 | Me | H | 8.215 | 7.401 |
| 143 | Me | H | 7.421 | |
| 144 | Me | H | 8.448 | |
| 145 | Me | H | 8.42 | 6.028 |
| 146 | Me | H | | |
| 147 | Me | H | 7.721 | |
| 148 | (CH2)3 | H | 7.863 | |
| 149 | Me | H | 8.959 | 7.883 |
| 151 | Me | H | 7.845 | |
| 152 | Me | Ph | 4.21 | |
| 153 | Me | NH2 | 6.749 | |
| 154 | Me | H | 8.009 | 6.262 |
| 155 | Me | H | 7.514 | |
| 157 | Me | H | 6.413 | |
| 158 | Me | H | 8.041 | 6.625 |
| 160 | Me | H | 8.678 | 7.177 |
| 161 | Me | H | 7.821 | 5.814 |
| 162 | Me | H | 5.418 | 5.026 |
| 163 | Me | H | 6.596 | 4.236 |
| 164 | Me | H | 7.618 | 6.505 |
| 165 | Me | H | 4.354 | <4 |
| 166 | Me | H | 5.693 | 4.518 |
| 167 | Me | H | 6.338 | 5.628 |
| 169 | Me | H | 7.101 | 5.771 |
| 170 | Me | H | 8.553 | 7.224 |
| 171 | Me | H | 5.895 | 4.74 |
| 173 | (CH2)4 | H | 8.086 | 6.469 |
| 174 | Me | H | 8.921 | 7.68 |
| 175 | Me | H | 8.921 | 7.717 |
| 176 | Me | H | 8.432 | 6.438 |
| 178 | Me | H | 7.873 | 6.461 |
| 180 | Me | H | 5.988 | |
| 181 | Me | H | 7.928 | |
| 183 | Me | H | 8.481 | |
| 184 | Me | H | 8.523 | 6.804 |
| 185 | Me | H | 8.749 | 7.433 |
| 187 | Me | H | 8.461 | 7.006 |
| 191 | Me | H | 8.097 | 7.563 |
| 192 | Me | H | 8.699 | 8.318 |
| 193 | Me | H | 8.481 | 7.245 |
| 195 | Me | H | 8.569 | 6.52 |
| 196 | Me | H | 8.411 | |
| 199 | Me | H | 7.924 | |
| 200 | Me | H | 8.42 | 5.95 |

TABLE 3-continued

| | | | | |
|---|---|---|---|---|
| 201 | Me | H | 6.585 | 7.231 |
| 203 | Me | H | 8.161 | |

What is claimed is:

1. A compound having the formula (1)

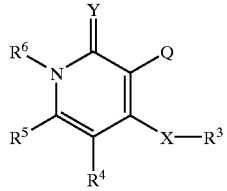

wherein:
Q represents —NR$_1$R$_2$ or —R$_0$NR$_1$R$_2$ wherein:
R$_0$ represents C$_{1-6}$ alkanediyl;
R$_1$ and R$_2$ each independently represent C$_{1-6}$ alkyl or C$_{3-6}$ alkenyl; said C$_{1-6}$ alkyl and C$_{3-6}$ alkenyl may be substituted with one, two or three substituents selected from the group consisting of hydroxy, C$_{1-4}$ alkyloxy, C$_{1-4}$ alkylthio, aryloxy, arylthio, amino, mono- and di(C$_{1-4}$alkyl)amino, and aryl;
R$_3$ represents aryl;
R$_4$ and R$_5$ each independently represent hydrogen, C$_{1-6}$ alkyl, C$_{3-6}$ alkenyl, C$_{1-4}$ alkoxy, C$_{1-4}$ alkoxyC$_{1-4}$ alkyl, amino, mono- or di(C$_{1-4}$alkyl)amino, formyl, C$_{1-4}$ alkylcarbonyl carboxyl, C$_{1-4}$ alkyloxycarbonyl, or C$_{1-4}$ alkyl aminocarbonyl; wherein C$_{1-6}$ alkyl and C$_{3-6}$ alkenyl may be substituted with one, two or three substituents selected from the group consisting of hydroxy, C$_{1-4}$ alkyloxy, C$_{1-4}$ alkylthio, aryloxy, arylthio, amino, mono- or di(C$_{1-4}$alkyl)amino and aryl;
R$_6$ represents hydrogen, hydroxy, C$_{1-4}$ alkyloxy, C$_{1-6}$ alkyl, C$_{3-6}$ alkenyl, aryl, C$_{1-4}$ alkyl, amino, mono- or di(C$_{1-4}$alkyl)amino or alkylaryl;
Y represents O or S;
X represents a radical of formula:

—(CH$_2$)$_p$  (a)

or

—(CH$_2$)$_q$—Z—(CH$_2$)$_r$  (b)

wherein
p represents 1, 2, 3, 4 or 5;
q represents 0, 1, 2, 3, 4 or 5;
r represents 0, 1, 2 or 3;
Z represents NR$_8$, C(=O), CHOH, CHNR$_8$R$_9$; CF$_2$, O, S or CH=CH; wherein R$_8$ and R$_9$ each independently represent hydrogen or C$_{1-4}$ alkyl; or
a N-oxide, a stereochemically isometric form or a pharmaceutically acceptable addition salt thereof, and
wherein aryl is phenyl or phenyl substituted with one, two or three substituents selected from the group consisting of C$_{1-4}$ alkyl, C$_{1-4}$ alkoxy, halo, and trifluoromethyl.

2. The compound according to claim 1, wherein R$_1$ and R$_2$ each represent a methyl group.

3. The compound according to claim 1, wherein X represents —CH$_2$— and R$_3$ represents a phenyl group substituted with two methyl groups.

4. The compound according to claim 1 which is 3-dimethylamino-4-(3,5-dimethylbenzyl)-5-ethyl-6-methylpyridin-2(1H)-one.

5. A process for obtaining a compound according to claim 1, wherein X represents —CH$_2$—, Y represents O, R$_3$ is an optionally-substituted phenyl group, and R$_6$ is hydrogen, said process comprising the following steps:
a) reacting a pyridine, substituted in position 2 with an alkoxy group and in position 3 with an amidoalkyl group, with a C$_1$–C$_6$ alkyllithium, to obtain a lithiated derivative of said pyridine;
b) reacting said lithiated derivative with a complex formed by CuI and dimethyl sulfide, to obtain an organocopper reagent;
c) reacting said organocopper reagent with an optionally substituted benzyl halide, to obtaining a protected pyridinone;
d) hydrolyzing said protected pyridinone, to obtain a deprotected pyridinone; and
e) substituting the amine-3 group of said deprotected pyridinone, to obtain said pyridinone compound.

6. A process for obtaining a compound according to claim 1, wherein X represents —C(=O), Y represents O, R$_3$ is an optionally substituted phenyl group, and R$_6$ is hydrogen, wherein said process comprises:
a) reacting a pyridine, substituted in position 2 with an alkoxy group and in position 3 with an amidoalkyl group, with a C$_1$–C$_6$ alkyllithium, to obtain a lithiated derivative of said pyridine;
b) reacting said lithiated derivative with an optionally substituted benzaldehyde, to obtain a substituted pyridinone;
c) oxidizing said substituted pyridinone, to obtain a protected pyridinone; and
d) deprotecting said protected pyridinone by hydrolysis, to obtain said pyridinone compound.

7. A pharmaceutical composition, comprising a therapeutically effective amount of at least one compound according to claim 1 and a pharmaceutical carrier.

8. The pharmaceutical composition of claim 7, wherein in said compound according to claim 1, R$_1$ and R$_2$ each represent a methyl group.

9. The pharmaceutical composition of claim 7, wherein in said compound according to claim 1, X represents —CH$_2$— and R$_3$ represents a phenyl group substituted with two methyl groups.

10. The pharmaceutical composition of claim 7, wherein said compound according to claim 1 is 3-dimethylamino-4-(3,5-dimethylbenzyl)-5-ethyl-6-methylpyridin-2(1H)-one.

11. A method for treating HIV-related disease wherein said method comprises a step of administering to a patient an effective amount of a compound according to claim 1.

12. The method of claim 11, wherein in said compound according to claim 1, R$_1$ and R$_2$ each represent a methyl group.

13. The method of claim 11, wherein in said compound according to claim 1, X represents —CH$_2$— and R$_3$ represents a phenyl group substituted with two methyl groups.

14. The method of claim 11, wherein said compound according to claim 1 is 3-dimethylamino-4-(3,5-dimethylbenzyl)-5-ethyl-6-methylpyridin-2(1H)-one.

15. A method for treating an HIV-infection, wherein said method comprises a step of administering to a patient an effective amount of a compound according to claim 1.

16. The method of claim 15, wherein in said compound according to claim 1, $R_1$ and $R_2$ each represent a methyl group.

17. The method of claim 15, wherein in said compound according to claim 1, X represents —$CH_2$— and $R_3$ represents a phenyl group substituted with two methyl groups.

18. The method of claim 15, wherein said compound according to claim 1 is 3-dimethylamino-4-(3,5-dimethylbenzyl)-5-ethyl-6-methylpyridin-2(1H)-one.

* * * * *